US00PP34288P2

(12) United States Plant Patent
Hansen

(10) Patent No.: US PP34,288 P2
(45) Date of Patent: May 31, 2022

(54) ***HEUCHERA* PLANT NAMED 'EVENING GOWN'**

(50) Latin Name: ***Heuchera* hybrid**
Varietal Denomination: Evening Gown

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,864

(22) Filed: Nov. 29, 2021

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80; A01H 5/02
See application file for complete search history.

*Primary Examiner* — Keith O. Robinson

(57) ABSTRACT

The new and distinct hybrid of *Heuchera* plant named 'Evening Gown' have cordate, moderately-dissected leaf blades of shiny purplish-black without any silvery overlay between the veins. The new plant has upright, branched panicles producing dense flowers. The new plant is vigorous and produces large clumps with many dense leaves and is useful in the landscape or in containers.

1 Drawing Sheet

Botanical denomination: *Heuchera* hybrid.
Variety denomination: 'Evening Gown'.

STATEMENT REGARDING PRIOR DISCLOSURES UNDER 37 CFR 1.77(B)(6)

The introduction of *Heuchera* 'Evening Gown' was in a non-enabling brief description and photograph on a website maintained by Walters Gardens, Inc. on Dec. 1, 2020. Subsequently, on May 21, 2021, Walters Gardens, Inc. introduced the new plant in the "Walters Gardens 2020-2021 Catalog" with a brief non-enabling description and photograph. The first sale of the new plant was by Walters Gardens, Inc. to Wojo's Greenhouse on Jul. 5, 2021. Walters Gardens, Inc. obtained the new plant and information about the new plant directly from the inventor. No plants of *Heuchera* 'Evening Gown' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Evening Gown'. 'Evening Gown' was hybridized by the inventor on Mar. 2, 2017 in the greenhouses of a wholesale perennial nursery in Zeeland, Mich., USA and assigned the breeder code 17-20-30. The seed or female parent was the proprietary, unreleased and unnamed hybrid assigned the breeder code 15-225-4 (not patented) and the male parent was 'Black Pearl' U.S. Plant Pat. No. 29,395.

*Heuchera* 'Evening Gown' was first selected in the fall of 2018 and passed final evaluation in the fall of 2019 from among thousands of other seedlings from the same cross and other crosses. 'Evening Gown' has been asexually propagated by basal shoot cuttings at the same nursery in Zeeland, Mich. in 2019 and by careful shoot tip tissue culture propagation, and the resultant plants have remained stable and continued to exhibit the same characteristics as the original plant for multiple generations.

BRIEF SUMMARY OF THE INVENTION

The following traits distinguish *Heuchera* 'Evening Gown' as a distinct hybrid plant. In comparison, the female parent has smaller and flatter leaves with less cupping and less wavy margins and the upper surface is not as shiny. The male parent is much smaller in habit and size, the leaves are lighter and more brown and the flowering is more profuse.

The most similar cultivars known to the inventor are: 'Obsidian' U.S. Plant Pat. No. 14,836, 'Timeless Night' U.S. Plant Pat. No. 32,134, 'Bella None' U.S. Plant Pat. No. 24,291, 'Black Taffeta' U.S. Plant Pat. No. 26,162 and 'Black Beauty' U.S. Plant Pat. No. 13,288.

'Obsidian' has smaller and flatter foliage with shallower incisions between the lobes. 'Timeless Night' has a more compact habit with smaller foliage that is flatter and less dissected between the lobes and the plant flowers more profusely. 'Bella Notte' has flatter leaves with no ruffling of the foliage, the top surface is not as shiny, the coloration is not as dark as the new plant and there is a slight silvery upper surface. 'Black Taffeta' has smaller leaves with less cupping and wavy margins. 'Black Beauty' has a smaller habit and smaller leaves and the foliage color tends to be more coppery-purple.

*Heuchera* 'Evening Gown' differs from its parents as well as all other coral bells known to the applicant in the following combined traits:

1. The large-sized, shiny, cordate, leaf blades are moderately dissected at five lobes;
2. Leaves have wavy margins and are cupped with base overlapping;

3. Leaves are deep purplish-black without any silvery overlay between the veins.
4. Leaves become purplish-bronze in the fall.
5. Produces large-sized clumps and many individual leaves.
6. Plant habit is vigorous and compact with medium height stems of dense flowers.

BRIEF DESCRIPTION OF THE DRAWINGS

The photograph of the new plant demonstrates the overall appearance of *Heuchera* 'Evening Gown' including the unique traits. The colors are as accurate as reasonably possible with modern color reproductions. Some slight variation of color may occur as a result of lighting quality, intensity, wavelength, and direction or reflection.

The figure shows a two-year-old plant late in the season.

DETAILED BOTANICAL DESCRIPTION

The following description is based on a two-year-old plant growing in a lightly shaded greenhouse and one-year-old plants in an outdoor partially shaded display garden in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 15-225-4, and the male or pollen parent was 'Black Pearl';

Plant habit: Hardy herbaceous perennial with basal rosette of foliage; mounded foliage about 40 cm tall and 26 cm in diameter with scapes to about 38 cm tall; stems to about 3.5 cm long and 3.5 cm diameter at base completely covered with petiole stipules, with about 30 leaves per stem and one main stem per plant;

Roots: Fibrous, finely branched; nearest RHS NN155B depending on soil type;

Growth rate: Vigorous, rapid; rooting from cutting in two weeks and finishing in three-liter container in about 3 months;

Foliage: Cordate; moderately penta-lobed (dissected about 35 mm), with basal lobes extending 50 mm beyond petiole and frequently imbricate to 30 mm; cupped to 40 mm deep centered around petiole; apex and major and minor lobe apices rounded and apiculate; base cordate; margin crenate and micro-ciliolate; bullate in the central region; adaxial and abaxial surfaces sparsely micro-puberulent, adaxial lustrous, abaxial moderately lustrous becoming matte; high number of leaf indentations with four major indentations and about 50 smaller indentations; leaf margin undulation strong;

Leaf blade size: To about 16.5 cm wide and 16.5 cm long, average about 13.0 cm wide and 12.5 cm long;

Leaf color: Seasonally variable; initial spring adaxial nearest 187A; initial spring abaxial nearest RHS N186C; adaxial leaves at near flowering nearest RHS N186A; abaxial leaves at near flowering between RHS N79A and RHS 187A; late season fall adaxial variable, nearest RHS N186A and RHS N189A; late season fall abaxial variable, between RHS N79B and RHS 187Bin some regions and between RHS 199D and RHS 161A in other patches;

Leaf quantity: Dense, about 30 per division and 100 per plant;

Veins: Palmate, hirsutulous abaxial and sparsely puberulent adaxial; costate abaxial and slightly concave adaxial;

Vein color: On emerging or early spring adaxial nearest RHS 187C; emerging or early spring abaxial nearest RHS N186D; near flowering season adaxial nearest RHS N186B with undertone of nearest RHS N189A; near flowering season abaxial proximal main veins between RHS N186B and RHS 182C and distally and secondary veins nearest RHS N186A; late season fall adaxial proximally nearest RHS 176A and distally between RHS 177A and RHS 187A; late season fall abaxial proximal between RHS 182D and RHS 155A; late season adaxial proximal main veins between RHS N186B and RHS 182C and distally and secondary veins nearest RHS N186A;

Petiole: Cylindrical; base amplexicaul; straight, stiff; outwardly with outer leaves and slightly upright with inner leaves; hirsute with hairs to about 2.0 mm long; to about 12.5 cm long and 7.0 mm across at base above stipule and 4.0 mm across below petiole, average about 11.0 cm long and about 5.5 mm across above stipule and 3.5 mm across below petiole;

Petiole color: Varying with season; young emerging leaf nearest RHS N186D; near flowering season adaxial nearest RHS N186C; late season fall nearest RHS N186C;

Stipule: At base of petiole; puberulent abaxial and glabrous adaxial; to about 19.0 mm long and about 22.0 cm wide at base and 20.0 mm wide at apex, with two distally-flared acute lobes about 7.0 mm long;

Stipule color: Adaxial center nearest RHS N79C and along edges nearest RHS 187A, abaxial ribs nearest RHS N79C and along edges nearest RHS 187A;

Peduncle: Panicle; cylindrical; stiff; puberulent to hirsute; upright; to about 75.0 cm long and 4.5 mm diameter at base, average about 70.0 cm tall and about 3.5 mm diameter; about seven per plant with up to 700 flowers per panicle, average about 500;

Inflorescence: Compound-branched panicle with up to 24 branches to about 6.0 cm long and about 1.0 mm diameter at base, decreasing in size distally, average 18 branches per panicle; branches outwardly to slightly upwardly becoming more outwardly distally; flower density is dense; flowering in upper 42.0 cm and 20.0 cm wide;

Flowering longevity: Panicle effective for about three weeks;

Flower density: Moderately dense;

Peduncle color: Distally nearest RHS 181A, proximally nearest RHS187C; branches nearest RHS 187C;

Pedicel: Cylindrical; finely puberulent, to about 3.0 mm long and 0.5 mm diameter;

Pedicel color: Between RHS 187A and RHS N186B;

Buds one day prior to opening: Oblong ellipsoidal; acute apex and attenuate base; puberulent; about 5.0 mm long and 3.0 mm diameter near middle;

Bud color one day prior to opening: Proximal portion nearest RHS 186A and distally nearest RHS 186D with the apex nearest RHS 138A;

Flower: Perfect, campanulate, actinomorphic, about 8.0 mm long to exserted style and 6.0 mm in diameter at face; corolla to 7.0 mm long and 6.0 mm diameter; individual flowers lasting about 4 days on plant or as cut flower; rarely persistent;

Flower attitude: Outwardly to slightly upwardly;

Calyx: Five sepals; apex acute; about 7.0 mm long and 5.0 mm wide, base fused in proximal 4.5 mm to form hypanthium;

Sepals: Five; puberulent to glandular abaxial, glabrous adaxial; rarely persistent;

Calyx color: Adaxial nearest RHS 182D with apex nearest RHS 138C, abaxial base between RHS 177D and RHS 182D and distally between RHS 182D and RHS 155A;

Petals: Five, linear to oblanceolate, acute apex and attenuate base; margin entire; glabrous abaxial and puberulent adaxial; adnate to adaxial sepals in proximal 0.5 mm; about 3.0 mm long and 1.0 mm wide near middle;

Petal color: Abaxial and adaxial nearest RHS NN155D;

Androecium: Five;

*Filaments*.—Five; glabrous; adnate to adaxial calyx about 1.0 mm above base; thin, glabrous; about 2.5 mm long and about 0.2 mm diameter; color nearest RHS NN155D.

*Anthers*.—Ellipsoidal, distinct, basifixed, longitudinal; about 0.5 mm long; color nearest RHS 25B.

*Pollen*.—Abundant; color nearest RHS 13C.

Gynoecium: One, two-beaked; half-inferior; 9.0 mm long;

*Style*.—Bifid; exserted; split apart at apex of ovary; about 5.0 mm long and about 0.5 mm diameter; color nearest RHS NN155C.

*Stigma*.—Acute apex, about 0.5 mm diameter; color nearest RHS 155A.

*Ovary*.—Half-inferior, about 3.0 mm long and 2.0 mm diameter; ellipsoidal to globose; apex acute, base rounded; color nearest RHS 145C.

Fruit: Two-beaked ellipsoidal capsule; about 4.5 mm long and 3.0 mm across; color nearest RHS 200B;

Seed: Thin ellipsoidal; less than 1.0 mm long and less than 0.5 mm wide; color between RHS 202A and RHS 200A;

Growth: 'Evening Gown' grows best with ample moisture and drainage in either sun or shade. Cold hardy from USDA zones 4 to 9.

Disease and pest tolerance: Resistance and tolerance outside of that normal for *Heuchera* is not known.

It is claimed:

1. The new and distinct *Heuchera* plant named 'Evening Gown' as herein described and illustrated.

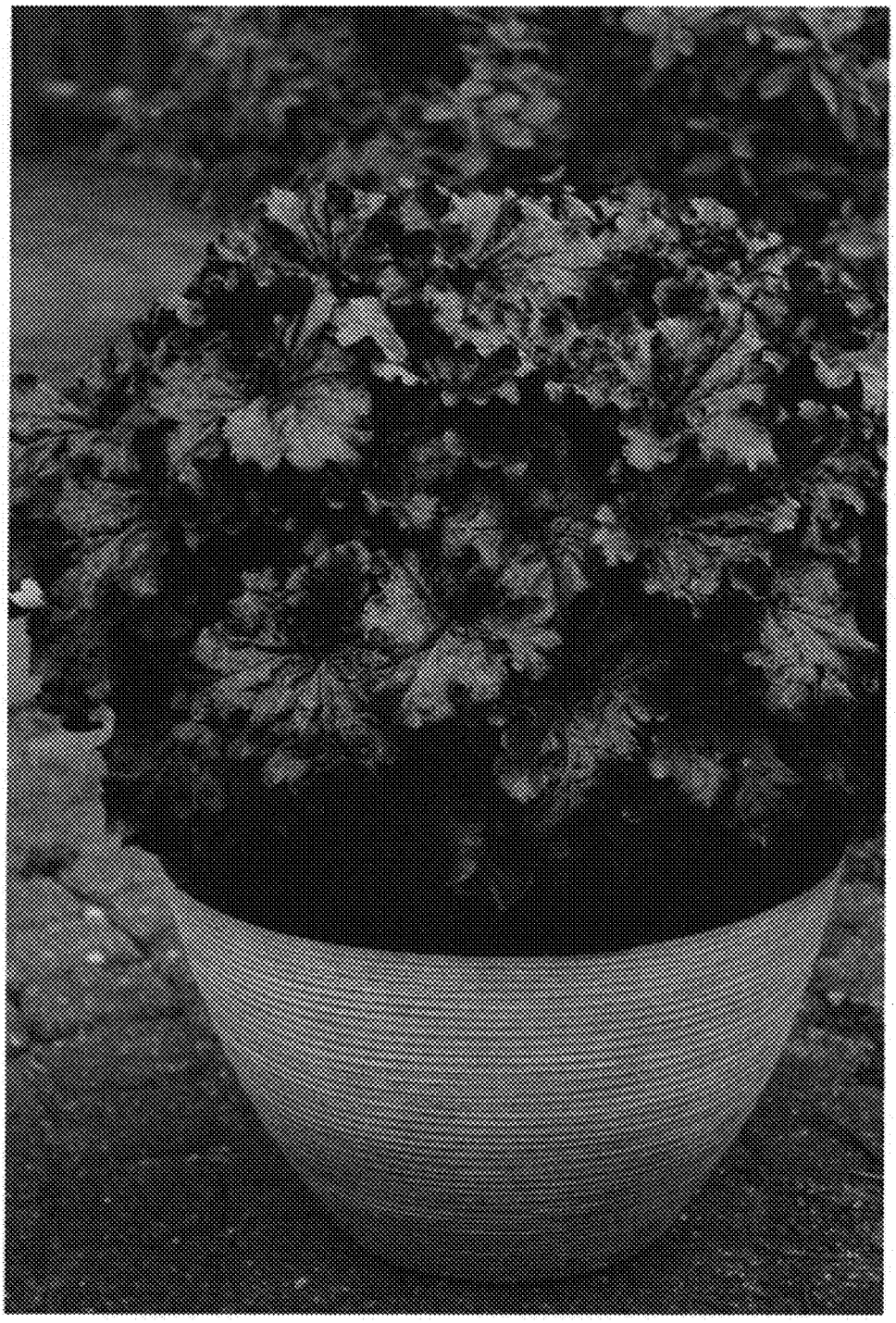

* * * * *